United States Patent [19]

Bouniot

[11] 3,988,313

[45] Oct. 26, 1976

[54] PROCESS FOR THE PRODUCTION OF FERMENTATION POLYSACCHARIDES HAVING A NON-FIBROUS STRUCTURE

[75] Inventor: Albert Bouniot, Bernier a Melle, France

[73] Assignee: Rhone-Poulenc S.A., Paris, France

[22] Filed: May 2, 1974

[21] Appl. No.: 466,462

[30] Foreign Application Priority Data

May 4, 1973  France .............................. 73.16148

[52] U.S. Cl. .................................. 536/1; 195/31 P
[51] Int. Cl.$^2$ ........................................ C08B 37/00
[58] Field of Search .................................. 260/209 R

[56] References Cited
UNITED STATES PATENTS

| | | | |
|---|---|---|---|
| 3,228,855 | 1/1966 | Cadmus et al. ................. | 260/209 R |
| 3,716,526 | 2/1973 | Schweiger ....................... | 260/209 R |
| 3,729,460 | 4/1973 | Patton ............................ | 260/209 R |

*Primary Examiner*—Johnnie R. Brown
*Attorney, Agent, or Firm*—Stevens, Davis, Miller & Mosher

[57] ABSTRACT

Polysaccharides produced by fermentation are obtained in a non-fibrous form by washing the product produced by precipitation from the fermentation medium with an aqueous organic liquid in which the proportion of organic liquid is high enough to give a washed product which is not soft, difficult to dry and with a tendency to agglomerate, but not so high that the washed product, after drying and grinding, has a fibrous structure, and then drying and grinding the washed polysaccharide.

7 Claims, No Drawings

PROCESS FOR THE PRODUCTION OF FERMENTATION POLYSACCHARIDES HAVING A NON-FIBROUS STRUCTURE

The present invention relates to the preparation, in a pulverulent non-fibrous form, of polysaccharides produced by fermentation of glucides with suitable microorganisms, for example, a species of Xanthomonas type, such as Xanthomonas campestris, or Arthrobacter such as Arthrobacter viscosus.

The polysaccharide is usually isolated from the fermentation medium by precipitation by adding a liquid precipitating agent to the medium, more particularly a water-miscible aliphatic alcohol, especially one of low molecular weight such as methanol, ethanol, isopropanol or tertiary butanol, or a water-miscible aliphatic ketone, e.g. acetone, or a mixture thereof, for example a mixture of tertiary butanol and acetone. The agent most commonly employed is isopropanol. Precipitation is generally effected with 45 to 60% by weight of precipitation agent in the medium.

The precipitated polysaccharide is generally in the form of rather long fibres. After they have been isolated from the mother liquors, they may be purified by washing, by agitating them in an appropriate aqueous organic washing liquid. This liquid is chosen so that the polysaccharide fibers are insoluble therein while the maximum amount of impurities are soluble. For simplicity, so far as possible the liquid used for this washing is chosen to be identical or at least similar to that used for the precipitation.

In these operations, it is customary to use alcohols or other organic liquids in the forms usually provided by industrial distillation, that is to say either in anhydrous form, or, more usually in the form of an aqueous azeotrope. Thus, for example, approximately 95.6% by volume ethanol, or approximately 87.8% by volume isopropanol are used.

The polysaccharide is then isolated from the washing liquid, dried and ground, for example to produce a powder, the particles of which have dimensions of between 50 and 400 μm.

However, the powder thus obtained usually possesses poor flow characteristics, its apparent density is low and it displays rather high compressibility. These properties cause great difficulties when the powder is transported and handled industrially, and give rise to various disadvantages, such as the powder becoming packed tightly in hoppers, or being easily carried away by the wind. These disadvantages are essentially due to the fact that the powder consists of small fibres.

It has now been found, according to the present invention, that it is possible to produce fermentation polysaccharides in the form of a powder which consists of small granules and which consequently has good flow characteristics. To achieve this result, it is necessary to use an aqueous organic washing liquid which contains neither too much nor too little water for washing the polysaccharide produced by precipitation from the fermentation medium.

In the text which follows, when the proportion by weight of organic liquid in the aqueous organic washing liquid is mentioned, this refers to the proportion by weight of the former in relation to the total of organic liquid + water. The organic liquid may be a single organic compound or a mixture of such compounds.

It has been found that if the washing liquid contains a proportion of the organic liquid below a certain level (referred to herein as a percentage or organic liquid $y$ % above the minimum percentage of the organic liquid at which the polysaccharide is insoluble), the polysaccharide fibres, after washing, are very soft, difficult to dry, and tend to agglomerate with one another.

On the other hand, if the washing liquid has more than a certain proportion of the organic liquid (referred to herein as a percentage of organic liquid $z$ % above the minimum percentage of the organic liquid at which the polysaccharide is insoluble) the product, after it has been washed, dried and ground, has a fibrous and not a granular structure.

Between these two limits (i.e, if the washing liquid contains a proportion by weight of organic liquid from $y$ % to $z$ % above the minimum percentage of the organic liquid at which the polysaccharide is insoluble), the polysaccharide is insoluble), the polysaccharide fibres, after washing, are easy to dry, and the product, after drying and grinding, is granular and not fibrous.

The present invention accordingly provides a process for the preparation, in a non-fibrous form, of a polysaccharide produced by fermentation, which comprises: precipitating the polysaccharide from the fermentation medium in which it has been produced by addition thereto of a water-miscible organic liquid in which the polysaccharide is insoluble; washing the precipitated polysaccharide with an aqueous organic liquid in which the proportion of the organic liquid is sufficiently above the minimum proportion at which the polysaccharide is insoluble to give a polysaccharide product with is not soft, difficult to dry and with a tendency to agglomerate, but not so much above the said proportion as to give a polysaccharide product which, after drying and grinding, has a fibrous structure; and then drying and grinding the washed polysaccharide.

Proportions of organic liquid higher than the proportion which corresponds to the solubility limit of the polysaccharide in the aqueous organic washing liquid are expressed herein in the following way: If $x$ % is the proportion by weight of organic liquid which corresponds to the solubility limit of the polysaccharide in the aqueous organic medium, and if the washing liquid is stated to contain, for example, a proportion by weight of organic liquid $w$ % which is 20% above the proportion $x$ %, then $w$ is equal, as a percentage, to $x + 20$ (and not $x$ plus 20% of $x$).

The need to have a restricted proportion of organic liquid to obtain a granular powder can be explained by the fact that the concentration of water which impregnates the solid polysaccharide is then sufficiently greater than its concentration in the surrounding liquid for the polysaccharide to form a gel again (a very thick gel), during the drying, since the organic liquid evaporates preferentially, and the fibrous structure of the polysaccharide is thus destroyed.

It can consequently be understood that, within the optimum zone for the proportion of organic washing liquid, as defined above, the exact optimum proportion depends on the configuration and the working conditions of the drier (e.g. whether it is worked continuously, discontinuously, or in vacuo).

The proportion of the organic liquid which corresponds to the solubility limit of the polysaccharide in the washing liquid varies depending on the circumstances, for example, on the nature of the washing liquid, and on the nature and the conditions of the fermentation. In practice, it must be determined beforehand for a given type of operation.

Likewise, it is necessary to determine beforehand, for a given type of operation, the correct range of proportions of organic liquid in the washing liquid, as defined above, as well as, where appropriate, the exact optimum proportion, because the values of these working factors are not the same for all washing liquids nor for all working conditions. In fact, they vary depending on diverse factors, and particularly on the nature of the washing liquid, the nature and conditions of the fermentation, the nature of the various bodies which can be adsorbed by the polysaccharide or bonded to it, the washing temperature, the concentration of solids in the washing zone, the period of contact with the washing liquid, the possible presence of foreign bodies (additives added for particular reasons), the conditions for carrying out the subsequent drying and grinding, and the final particle size.

For a given organic washing liquid, in order to find the optimum range of proportions by weight of this agent (between $y$ % and $z$ % above the proportion which corresponds to the solubility limit of the polysaccharide in the washing liquid), it is advisable to carry out prior tests. It is convenient and effective to carry out these tests in the manner described in paragraphs a) and b) below:

a. If an organic washing liquid, which can also be used to precipitate the polysaccharide from the fermentation liquid, is to be used, the solubility limit of the polysaccharide is first determined by making a gel, for example containing approximately 1% by weight of the polysaccharide in distilled water, and the introducing, over the course of less than 5 minutes, the organic washing liquid under investigation into a volume of approximately 2 liters of this gel, which is kept at the desired temperature and is stirred, until the polysaccharide precipitates. It is then easy to calculate the concentration of water relative to the total of water + organic liquid when precipitation occurs. A second similar test is preferably carried out thereafter, which makes it possible to determine the concentration of organic liquid with more precision.

b. In a second stage, parallel tests of washing the freshly drained, precipitated polysaccharide are carried out, using, as the washing liquids for the various parallel tests, mixtures of water and the organic washing liquid. These mixtures contain gradually increasing proportions of the organic liquid, for example, proportions of 5%, 10%, 15%, 20%, 25% and the like respectively (or, alternatively, gradually decreasing proportions of water relative to the total of water + organic agent, which makes it possible to know the corresponding proportions of the latter), above the proportion by weight of organic washing liquid corresponding to the solubility limit as determined by the test a. These washing processes are effected using the working conditions (temperature, concentration of dry material, period of contact and the like) which it is proposed to use in practice. The product obtained after each washing test is isolated, drained, dried, ground and optionally screened, all of these processes being carried out under the conditions and with the type of equipment which it is proposed to employ in practice. The particles obtained in each test are examined under a microscope and their flow characteristics are measured, preferably be means of a test such as that described in Example 1 below. The optimum working conditions to be employed in the washing process, as a function of the other conditions of the entire process for the production of the polysaccharides, are thus determined.

For example, if isopropanol is used as the organic washing liquid, it is found that generally the value $x$ % of the proportion by weight of this liquid which corresponds to the solubility limit of the polysaccharide in the washing medium is about 50%, the value of $y$ % above this proportion is approximately 8% and the value of $z$ % above this porportion is approximately 25%. The exact optimum value for aqueous isopropanol to be used as the washing liquid thus lies between 8% and 25% by weight above the proportion by weight of this alcohol which corresponds to the solubility limit of the polysaccharide in the washing medium.

Other tests using tertiary butanol as the organic washing liquid have shown a value $x$ % of the proportion by weight of this agent which corresponds to the solubility limit of the polysaccharide in the washing medium, of the order of 50%, a value of $Y$ % above this proportion, of approximately 9%, and a value of $z$ % above this proportion, of approximately 28%. Thus, the exact optimum value for aqueous tertiary butanol to be used as the washing liquid lies between 9% and 28% by weight above the proportion by weight of this alcohol which corresponds to the solubility limit of the polysaccharide in the washing medium.

The preferred general conditions for operating the process of the present invention are as follows:

The washing process is preferably carried out at a temperature of 0° to 50° C, and more particularly at a temperature of 25° to 35° C, the period of contact of the polysaccharide with the washing liquid being from 3 minutes to 1 hour. The washing liquid also preferably contains, as the organic washing agent, either an alcohol of low molecular weight such as methanol, ethanol, isopropanol or tertiary butanol, or, instead of a single alcohol, a mixture of such alcohols with one another and/or with at least one other organic liquid such as acetone, or a suitable non-alcoholic organic liquid, for example a water-miscible ketone such as acetone alone, or a mixture of such non-alcoholic organic liquids. It is particularly convenient for the organic washing liquid to be identical to the organic liquid used to bring about precipitation.

It is immaterial what procedure is employed for carrying out the washing. It is possible, for example, to work continuously or discontinuously, and to use a tank with mechanical stirring or a counter-current apparatus with systematic contact. The proportion of washing liquid should be at least 5 kg, and more particularly 40 to 150 kg, or even more, per kg of polysaccharide.

The organic washing liquid can be recovered by distilling the liquid resulting from the washing process using conventional techniques. Where this liquid is a single alcohol, it is possible to adjust the distillation in such a way that the alcohol is recovered with the necessary proportion of water so that it can be reused directly for another washing operation. However, it is usually simpler to recover the alcohol in the concentrated form which is usual in industry, and then to dilute it to the desired proportion by adding water. For this purpose, distilled water, spring water or water to which certain compounds have been added to fulfill specific objectives additional to the aim of the present invention, are preferably used; for example, it is possible to add to the water a decolourising agent.

Where the organic washing liquid comprises several organic compounds, distillation of the liquid from the washing process can make it possible to recover these compounds mixed together if their volatilities are similar (which is the case, for example, for a mixture of methanol and acetone), or separately if their volatilities are markedly dissimilar, in which case they can be remixed with one another for further use (which is the case, for example, for a mixture of tertiary butanol and acetone). Nevertheless, in either case the usual procedure is to recover the compounds not in the aqueous form with the necessary proportion of water to enable them to be reused directly for another washing operation, but in their concentrated form which is usual in industry. The compounds are subsequently mixed and rediluted in the desired proportions, for further use. This dilution is carried out in accordance with the principles given above.

The following Examples illustrate the invention.

EXAMPLE 1

Test A. 10 liters of a fermentation medium, produced by the fermentation of an aqueous medium containing sugar by *Xanthomonas campestris*, are placed in a tank equipped with a mechanical stirrer (turbine). [The aqueous medium contained 20 g of sucrose per liter and was fermented for 60 hours.] The fermentation medium is stirred with the turbine at 500 revolutions/minute, at a temperature of 25° C, and 21 liters of aqueous isopropanol at 25° C, with an alcohol content of 83% by weight (density: 0.822), are introduced into it over the course of 5 minutes, still with stirring, which causes the polysaccharide to be precipitated in the form of fibres. The proportion of isopropanol which corresponds to the solubility limit of the polysaccharide in the precipitation medium is, in this case, approximately 53% by weight.

The fibrous polysaccharide precipitate is filtered off and returned to the tank into which 10 liters of 83% isopropanol are introduced as washing liquid. This method of working is not in accordance with the present invention, because the proportion by weight of isopropanol in the washing liquid is greater by approximately 30% (= 83 − 53) than that which corresponds to the solubility limit of the polysaccharide. It is found, in fact, by carrying out suitable experiments, that its solubility limit in the washing medium is similar to that in the precipitation medium.

The contents of the tank are stirred at 500 revolutions/minute for 10 minutes and the washed polysaccharide is then filtered off. The fibres obtained are spread over a drier hurdle and dried for half an hour at a temperature of 85° C in a stream of air. 140 g of polysaccharide with a moisture content of not more than 7% are thus obtained. It is reduced to a powder in a grinder with a 1 mm grid. The final whitish powder has an apparent density of 0.42 in the non-compressed state and 0.57 in the compressed state. If 50 cm$^3$ thereof are introduced into a bottle of diameter 30 mm, pierced at its lower end with a circular orifice of 5 mm diameter, this orifice allows only about 1 cm$^3$ of the powder to flow through, without shaking. Microscopic examination at a magnification of 50 shows that the powder consists of small fibres.

Test B. The fibrous polysaccharide is precipitated, in the same way as in Test A, from 10 liters of the same fermented liquid.

After the precipitate has been filtered off for the first time, it is returned to the tank into which 10 liters of 65% isopropanol (density at 25° C: 0.870), produced by diluting 83% isopropanol with water, are also introduced. This method corresponds to the technique of the present invention, the proportion of alcohol by weight in the washing liquid being only about 12% (= 65 −53) higher than that which corresponds to the solubility limit of the polysaccharide.

Stirring, draining and drying are carried out as in Test A. The polysaccharide obtained has a moisture content of 7%. It is ground as in Test A. The final whitish powder has an apparent density of 0.66 in the non-compressed state and 0.83 in the compressed state. If it is subjected to the flow test described in Test A, the orifice of the bottle allows approximately 40 cm$^3$ of the powder to flow through, without shaking. Microscopic examination at a magnification of 50 shows that the powder consists of small granules, resembling powdered glass.

EXAMPLE 2

Test C. 10 liters of a fermentation medium, produced by the fermentation of an aqueous medium containing glucose by *Arthrobacter viscosus*, are placed in a tank equipped with a mechanical stirrer (turbine). [The aqueous medium contained 15 g of glucose per liter and was fermented for 90 hours.] The fermentation medium is stirred with the turbine at 500 revolutions/minute, at a temperature of 25° C, and 10 kg of 25° C aqueous tertiary butanol, with an alcohol content of 96.5% by weight, are introduced into it over the course of 5 minutes, still with stirring, which causes the polysaccharide to be precipitated in the form of fibres. The proportion of tertiary butanol which corresponds to the solubility limit of the polysaccharide in the precipitation medium is, in this case, approximately 49% by weight.

The precipitated polysaccharide is then treated as described in Example 1, Test A, with the difference that the washing process is carried out with 96.5% tertiary butanol instead of 83% isopropanol. This is a washing technique which is not in accordance with the present invention, since the proportion by weight of tertiary butanol in the washing liquid is about 47.5% (= 96.5 − 49) higher than that which corresponds to the solubility limit of the polysaccharide. As in Example 1, tests show that its solubility limit in the washing medium is similar to that in the precipitation medium.

89 g of polysaccharide powder with a moisture content of not more than 5% are finally obtained. This powder, in the non-compressed state, has an apparent density of 0.35 and its flow characteristics are very poor, just as in Test A of Example 1. This powder consists of small fibres.

Test D. The fibrous polysaccharide is precipitated in the same way as in Test C from 10 liters of the same fermented medium.

The precipitate is treated as described in Example 1, Test B, with the difference that the washing process is carried out with 65% tertiary butanol instead of 65% isopropanol. This method of working corresponds to the technique of the present invention, the proportion by weight of alcohol in the washing liquid being only about 16% (= 65 − 49) higher than that which corresponds to the solubility limit of the polysaccharide.

93 g of polysaccharide powder with a moisture content of 8% are finally obtained. This powder, in the non-compressed state, has an apparent density of 0.74 and its flow characteristics are good, just as in Test B of Example 1. This powder consists of small granules.

I claim:

1. In a process for the preparation of a fermentation polysaccharide produced by fermentation with *Xanthomonas campestris* or *Arthrobacter viscosus* by precipitating the polysaccharide from the aqueous fermentation medium in which it has been produced by addition thereto of a watermiscible organic liquid in which the polysaccharide is insoluble and then drying and grinding the precipitated polysaccharide; the improvement which consists in washing the precipitated polysaccharide before it is dried with a washing liquid which is a mixture of water and an organic liquid miscible therewith selected from the class consisting of water-miscible lower alcohols, water-miscible aliphatic ketones and their mixtures in which the proportion of the organic liquid in the washing liquid is such that the polysaccharide product, after washing, drying and grinding, is obtained in the form of a powder consisting of small granules having good flow characteristics.

2. The improvement of claim 1, in which the said organic liquid is methanol, ethanol, isopropanol, tertiary butanol, acetone, or a mixture thereof.

3. The improvement of claim 1, in which the precipitated polysaccharide is washed with aqueous isopropanol containing from 8% to 25% more isopropanol than the minimum percentage required to precipitate the polysaccharide.

4. The improvement of claim 1, in which the precipitated polysaccharide is washed with aqueous tertiary butanol containing from 9% to 28% more tertiary butanol than the minimum percentage required to precipitate the polysaccharide.

5. The improvement of claim 1, in which the polysaccharide is washed at 0° to 50° C.

6. The improvement of claim 1, in which the period of contact of the polysaccharide with the washing liquid is 3 minutes to 1 hour.

7. The improvement of claim 1, in which 5 to 150 kg of the washing liquid are employed per kg of polysaccharide.

* * * * *